United States Patent [19]

Klar et al.

[11] Patent Number: 5,023,273
[45] Date of Patent: Jun. 11, 1991

[54] 6-OXOPROSTAGLANDIN E DERIVATIVES, PROCESS FOR THEIR PRODUCTION AND THEIR PHARMACEUTICAL USE

[75] Inventors: Ulrich Klar; Werner Skuballa; Helmut Vorbrüggen; Claus-Steffen Stürzebecher; Karl-Heinz Thierauch; Ekkehard Schillinger, all of Berlin, Fed. Rep. of Germany

[73] Assignee: Schering Aktiengesellschaft, Berlin and Bergkamen, Fed. Rep. of Germany

[21] Appl. No.: 276,502
[22] PCT Filed: Mar. 11, 1988
[86] PCT No.: PCT/DE88/00151
§ 371 Date: Nov. 23, 1988
§ 102(e) Date: Nov. 23, 1988
[87] PCT Pub. No.: WO88/07037
PCT Pub. Date: Sep. 22, 1988

[30] Foreign Application Priority Data

Mar. 13, 1987 [DE] Fed. Rep. of Germany ....... 3708537

[51] Int. Cl.$^5$ .................. C07C 177/00; A61K 31/557
[52] U.S. Cl. .................... 514/530; 514/573; 560/121; 562/503
[58] Field of Search ................. 560/121; 562/503; 514/530, 573

[56] References Cited

U.S. PATENT DOCUMENTS

| | | | |
|---|---|---|---|
| 4,205,178 | 5/1980 | Axen | 560/121 |
| 4,235,930 | 11/1980 | Skuballa | 560/121 |
| 4,315,013 | 2/1982 | Skuballa | 560/121 |
| 4,560,786 | 12/1985 | Skuballa | 560/121 |
| 4,783,480 | 11/1988 | Wakatsuka | 514/423 |

FOREIGN PATENT DOCUMENTS 2108960 5/1980 United Kingdom ................ 560/921

Primary Examiner—Robert Gerstl
Attorney, Agent, or Firm—Millen, White & Zelano

[57] ABSTRACT

The invention relates to 6-oxo-prostaglandin $E_1$ derivatives of formula I,

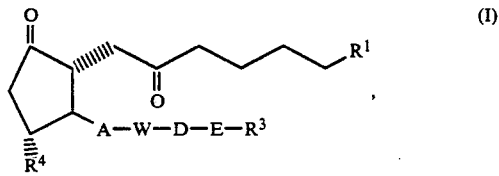

in which
$R^1$ means the radical $COOR^2$ with $R^2$ meaning a hydrogen atom, $C_1$-$C_{10}$ alkyl, a $C_5$-$C_6$ cycloalkyl or a $C_6$-$C_{10}$ aryl group or a heterocyclic radical, or the radical $CONHSO_2\ R^5$ as $C_{1-10}$ alkyl, $C_{5-6}$ cycloalkyl or $C_{6-10}$ aryl, A means an E-configuration CH=CH or a —C≡C group, W means a free or functionally modified hydroxymethylene group or a free or functionally modified group, and the OH group in each case can be in the alpha or beta position, D means a straight-chain or branched-chain alkylene group with 1-5 C atoms, E means a —C≡C group or a $C_2$-$C_4$ alkenylene group, $R^3$ means $C_1$-$C_{10}$ alkyl, $C_3$-$C_{10}$ cycloalkyl or an optionally substituted $C_6$-$C_{10}$ aryl group or a heterocyclic group, $R^4$ means a free or functionally modified hydroxy group, and if $R^2$ means a hydrogen atom, its salts with physiologically compatible bases as well as alpha, beta or gamma cyclodextrin clathrates of the compounds of formula I, process for their production and their pharmaceutical use.

8 Claims, No Drawings

6-OXOPROSTAGLANDIN E DERIVATIVES, PROCESS FOR THEIR PRODUCTION AND THEIR PHARMACEUTICAL USE

The invention relates to new 6-oxo-prostaglandin E derivatives, process for their production as well as their use as pharmaceutical agents.

From the very voluminous prior art of prostaglandins, especially of the E type and their analogs, it is known that this substance class because of its biological and pharmacological properties is suitable for therapy and prophylaxis of thromboses, infarcts and other cardiovascular diseases. Structural changes therefore have the aim of extending the duration of action, of increasing the selectivity of the effectiveness and at the same time of reducing the effective dose.

It has now been surprisingly found that by the introduction of a three-fold bond in the 18, 19 or 19, 20 and/or 13, 14 position as well as the introduction of a methyl group in the 16 and/or 20 position of the lower chain of the 6-oxo-prostaglandin $E_1$ analogs the effectiveness can be improved, the selectivity increased and the duration of action extended.

The compounds according to the invention act for inhibition of thrmobocyte aggregation, reduction of blood pressure and for vasodilation and bronchodilation. They are also suitable for inhibition of gastric acid secretion as well as cytoprotection on stomach, heart, liver, pancreas and kidneys.

The invention relates to 6-oxo-prostaglandin $E_1$ derivatives of formula I,

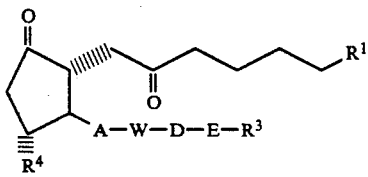

in which
$R^1$ means the radical $COOR^2$ with $R^2$ meaning a hydrogen atom, a $C_1$–$C_{10}$ alkyl, a $C_5$–$C_6$ cycloalkyl or a $C_6$–$C_{10}$ aryl group or a heterocyclic radical, or the radical $CONHSO_2R^5$ with $R^5$ as $C_{1-10}$ alkyl, $C_{5-6}$ cycloalkyl or $C_{6-10}$ aryl,
A means an E-configured CH=CH or a —C≡C group,
W means a free or functionally modified hydroxymethylene group or a free or functionally modified

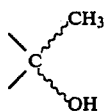

group, and the OH group can be in the alpha or beta position, respectively,
D means a straight-chain or branched-chain alkylene group with 1–5 C atoms, and
E means a —C≡C group or a $C_2$–$C_4$ alkenylene group,
$R^3$ means $C_1$–$C_{10}$ alkyl, $C_3$–$C_{10}$ cycloalkyl or an optionally substituted $C_6$–$C_{10}$ aryl group or a heterocyclic group,
$R^4$ means a free or functionally modified hydroxy group, and if $R^2$ means a hydrogen atom, its salts with physiologically compatible bases as well as alpha, beta or gamma cyclodextrin clathrates of the compounds of formula I.

As alkyl groups $R^2$ and $R^5$ are understood straight-chain or branched-chain alkyl groups with 1–10 carbon atoms such as, for example, methyl, ethyl, propyl, isopropyl, butyl, isobutyl, tertbutyl, pentyl, isopentyl, neopentyl, heptyl, hexyl, decyl.

The alkyl groups $R_2$ can optionally be substituted once or several times by halogen atoms, hydroxy groups, $C_1$–$C_4$ alkoxy groups, optionally substituted $C_6$–$C_{10}$ aryl groups, di-$C_1$–$C_4$ alkylamines and tri-$C_1$–$C_4$ alkyl ammonium. Those alkyl groups that are substituted once are preferred.

As substituents there can be mentioned, for example, fluorine, chlorine or bromine atoms, phenyl, dimethylamino, diethylamino, methoxy, ethoxy.

There can be mentioned as preferred alkyl groups $R^2$ those with 1–4 carbon atoms such as, for example, methyl, ethyl, propyl, dimethylaminopropyl, isobutyl and butyl.

As aryl groups $R^2$ and $R^5$ both substituted and unsubstituted aryl groups are suitable such as, for example, phenyl, alpha or beta naphthyl. These groups can be substituted by 1–3 halogen atoms, a phenyl group, 1–3 alkyl groups with 1–4 carbon atoms each, a chloromethyl, fluoromethyl, trifluoromethyl, carboxyl, hydroxy or alkoxy group with 1–4 carbon atoms. Substituents in the 3 and 4 position on the phenyl ring, e.g., by fluorine, chlorine, alkoxy or trifluoromethyl or the 4 position by hydroxy are preferred.

The cycloalkyl groups $R^2$ and $R^5$ can contain 5 and 6 carbon atoms in the ring. The rings can be substituted by alkyl groups with 1–4 carbon atoms. As examples there can be mentioned cyclopentyl, cyclohexyl, methylcyclohexyl and adamantyl.

5- or 6-membered heterocycles are suitable as heterocyclic groups $R^2$, which preferably contain a heteroatom, preferably nitrogen, oxygen or sulfur. There can be mentioned as examples 2-furyl, 3-furyl, 2-thienyl, 3-thienyl, 2-pyridyl, 3-pyridyl and 4-pyridyl.

The hydroxy groups $R^4$ and in W can be functionally modified, for example by etherification or esterification, and the free or modified hydroxy groups in W can be in the alpha or beta position and free hydroxy groups are preferred.

Radicals known to one skilled in the art are suitable as ether and acyl radicals. Easily cleavable ether radicals, such as, for example, the tetrahydropyranyl, tetrahydrofuranyl, methoxymethyl, methoxy ethyl, tert-butyl-dimethylsilyl, tert-butyl-diphenylsilyl, hexyl-dimethylsilyl and alpha-tribenzylsilyl radical are preferred. As acyl radicals there can be mentioned, for example, acetyl, propionyl, butyryl and benzoyl.

Straight-chain or branched-chain, saturated and unsaturated alkyl radicals, preferably saturated, with 1–10, especially 1–7 C atoms are suitable as alkyl group $R^3$, which optionally can be substituted by optionally substituted aryl. As examples there can be mentioned methyl, ethyl, propyl, butyl, isobutyl, tert-butyl, pentyl, hexyl, heptyl, octyl, butenyl, isobutenyl, propenyl, pentenyl, hexenyl, benzyl and p-chlorobenzyl.

The cycloalkyl group $R^3$ can contain 3–10, preferably 3–6 carbon atoms in the ring. The rings can be substituted by alkyl groups with 1–4 carbon atoms. As examples there can be mentioned cyclopropyl, cyclobutyl, cyclopentyl, cyclohexyl, methylcyclohexyl and adamantyl.

As substituted or unsubstituted aryl groups $R^3$ there are suitable, for example, phenyl, 1-naphthyl and 2-naphthyl, which, in each case, can be substituted by 1-3 halogen atoms, a phenyl group, 1-3 alkyl groups with 1-4 carbon atoms each, a chloromethyl, fluoromethyl, trifluoromethyl, carboxyl, $C_1$-$C_4$ alkoxy or hydroxy group. Substitution in the 3 and 4 position on the phenyl ring are preferred, e.g., by fluorine, chlorine, $C_1$-$C_4$ alkoxy or trifluoromethyl or in the 4 position by hydroxy.

Suitable as heterocyclic groups $R^3$ are 5- and 6-membered heterocycles, which contain at least 1 heteroatom, preferably nitrogen, oxygen or sulfur. As examples there can be mentioned 2-furyl, 3-furyl, 2-thienyl, 3-thienyl, 2-pyridyl, 3-pyridyl and 4-pyridyl.

Suitable as alkylene group D are straight-chain or branched-chain, saturated and unsaturated alkylene radicals, preferably saturated with 1-10, especially 1-5, carbon atoms, which optionally can be substituted by fluorine atoms. As examples there can be mentioned methylene, fluoromethylene, ethylene, 1,2-propylene, ethylethylene, trimethylene, tetramethylene, pentamethylene, 1-methyltetramethylene and 1-methyltrimethylene.

For salt formation with the free acids ($R^2$=H) inorganic and organic bases are suitable, as they are known to one skilled in the art for the formation of physiologically compatible salts. As examples there can be mentioned alkali hydroxides such as sodium and potassium hydroxide, alkaline earth hydroxides such as calcium hydroxide, ammonia, amines such as ethanolamine, diethanolamine, triethanolamine, N-methylglucamine, morpholine-, tris-(hydroxymethyl)-methylamine, etc.

E as $C_2$-$C_4$ alkylene group comprises the following radicals: —CH=CH, —CH=C(CH$_3$)—, —C(CH$_3$)=CH or —C(CH$_3$)=C(CH$_3$)—.

The invention further relates to a process for production of the compounds of formula I, which is characterized in that a compound of the formula II

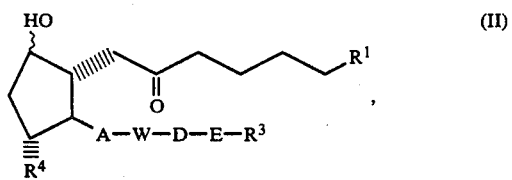

in which $R^1$, $R^3$, $R^4$, A, W, D and E exhibit the above-indicated meanings and free OH groups in $R^4$ and W are protected, is oxidized with the reagent chromosulfuric acid (Jones Reagent, J. Chem. Soc. 1953, 2555), pyridinium dichromate (Tetrahedron Lett. 1979, 399), pyridinium chlorochromate (Tetrahedron Lett. 1975, 2647), Collins reagent or complexes of $CrO_3$ with other amine bases such as, for example, pyrazole and benzotriazole to a compound of formula I and optionally hydroxy groups are released and/or free hydroxy groups are esterified, etherified and/or esterified carboxy groups are saponified or a carboxy group with a physiologically compatible base is converted into a salt or with alpha, beta or gamma cyclodextrin is converted into a clathrate.

The reaction of the compounds of general formula II to the compounds of general formula I is performed with Jones reagent at −40° C. to 0° C., preferably at −30° C. to −10° C., using other oxidation processes preferably at −10° C. to +25° C. Methylene chloride, chloroform, ethylene chloride, acetone, pyridine, i.a., but preferably methylene chloride and acetone, are suitable as solvents.

Release of the functionally modified hydroxy groups $R^4$ and in W to the compounds of general formula I takes place according to methods known to one skilled in the art. For example, cleavage of ether protecting groups is performed in an aqueous solution of an organic acid, such as, e.g., acetic acid, propionic acid, citric acid, i.a., or in an aqueous solution of an inorganic acid, such as, e.g., hydrochloric acid, or if in the case of tetrahydropyranyl ethers using pyridinium p-toluenesulfonate, preferably in alcohols as solvent or using anhydrous magnesium bromide, preferably in diethyl ether as solvent.

To improve the solubility when aqueous acidic reaction conditions are used, a water-miscible inert solvent is suitably added. There have proved suitable, e.g., alcohols such as methanol and ethanol, ethers such as dimethoxyethane, dioxane and tetrahydrofuran, and tetrahydrofuran is preferably used.

Cleavage of silyl ether protecting groups takes place, for example, with tetrabutyl ammonium fluoride. For example, tetrahydrofuran, diethyl ether, dioxane, methylene chloride, etc., are suitable as solvents.

Cleavage is preferably performed at temperatures between 20° C. and 80° C.

Saponification of the acyl groups and prostaglandin esters is performed according to methods known to one skilled in the art, as, for example, with basic catalysts such as, e.g., alkali or earth alkali carbonates or hydroxides in an alcohol or in the aqueous solution of an alcohol. Aliphatic alcohols, such as, e.g., methanol, ethanol, butanol, etc., but preferably methanol, are suitable as alcohols. Potassium and sodium salts can be mentioned as alkali carbonates and hydroxides. Potassium salts are preferred. Calcium carbonate, calcium hydroxide and barium carbonate, for example, are suitable as earth calcium carbonates and hydroxides. The reaction generally takes place at −10° C. to +70° C., but preferably at +25° C.

The introduction of the ester group $CO_2R^2$ for $R^1$, in which $R^2$ represents an alkyl group with 1-10 C atoms, takes place according to methods known to one skilled in the art. The 1-carboxy compounds ($R^2$=H) are reacted, for example, with diazo hydrocarbons in a way known in the art. Esterification with diazo hydrocarbons takes place, e.g., by a solution of the diazo hydrocarbon in an inert solvent, preferably in diethyl ether, being mixed with the 1-carboxy compound, dissolved in the same or in another, also inert, solvent, such as, e.g. methylene chloride. After the reaction is completed in 1 to 60 minutes, the solvent is removed and the ester is purified in the usual way. Diazoalkanes are either known or can be produced according to known methods [Org. Reactions, Vol. 8, pp. 389–394 (1954)].

Introduction of the amide group $CONHSO_2R^5$ for $R_1$ takes place according to methods known to one skilled in the art. The carboxylic acids of general formula I ($R_2$=H) are first converted in the presence of a tertiary amine, such as, for example, triethylamine, with chloroformic acid isobutyl ester, into the mixed anhydride. The reaction of the mixed anhydride with the alkali salt of the corresponding amide or with ammonia ($R_3$=H) takes place in an inert solvent or solvent mixture, such as, for example, tetrahydrofuran, dimethoxyethane, dimethylformamide, hexamethylphosphoric acid triamide, at temperatures between −30° C. and +60° C., preferably at 0° C. to 30° C.

Introduction of the ester group $CO_2R^2$ for $R^1$, in which $R^2$ represents a substituted or unsubstituted aryl group, takes place according to method known to one skilled in the art. For example, the 1-carboxy compounds are reacted with the corresponding aryl hydroxy compounds with dicyclohexylcarbodiimide in the presence of a suitable base, such as, e.g., pyridine, dimethylaminopyridine, triethylamine, in an inert solvent such as, e.g., methylene chloride, ethylene chloride, chloroform, ethyl acetate, tetrahydrofuran, but preferably chloroform. The reaction is performed at temperatures between −30° C. and +50° C., preferably at +10° C.

The prostaglandin derivatives of formula I with $R^1$ meaning a hydrogen atom can be converted into salts with suitable amounts of the corresponding bases with neutralization. For example, the solid inorganic salt is obtained by dissolving the corresponding prostaglandin acids in water, which contains stoichiometric amounts of the base, after evaporation of the water or after addition of a water-miscible solvent, e.g., alcohol or acetone.

Production of the amine salts takes place in the usual way. For this purpose, the prostaglandin acid is dissolved in a suitable solvent, such as, e.g., ethanol, acetone, diethyl ether or benzene and 1 to 5 equivalents of the respective amine is added to this solution. In this case, the salt is usually precipitated in solid form or isolated in the usual way after evaporation of the solvent.

The functional modification of the free hydroxy groups takes place according to methods known to one skilled in the art. For introduction of the ether protecting groups, reaction is performed, for example, with dihydropyran or methyl vinyl ether in methylene chloride or choloroform using catalytic amounts of an acidic condensation agent, such as, e.g., p-toluenesulfonic acid. The respective enol ether is added in excess, preferably in 1.5 to 10 times the amount of the theoretical requirement. The reaction takes place normally at −10° C. to +30° C. and is ended after 2–30 minutes.

Introduction of the acyl protecting groups takes place by a compound of formula I being reacted in a way known in the art with a carboxylic acid derivative, such as, e.g., acid chloride, acid anhydride, etc.

The compounds of general formula cause lowering of blood pressure and bronchodilation. They are suitable for inhibition of thrombocyte aggregation, act cytoprotectively on the stomach, liver, kidneys and pancreas and therefore can be used for organ transplantations. Consequently the new 6-oxo-prostaglandin E derivatives represent valuable pharmaceutical agents. Moreover, with a similar range of action, they exhibit a higher specificity and more extended duration of action, in comparison with corresponding prostaglandins.

The new prostaglandin analogs have the properties typical for prostaglandin E, such as, e.g., reduction of the peripheral arterial and coronary vascular resistance, inhibition of thrombocyte aggregation and dissolution of platelet thrombi, mycocardial cytoprotection and thus reduction of the systemic blood pressure without reducing at the same time cardiac output and coronary blood flow; other indications in principle can be: stroke, prophylaxis and therapy of coronary diseases, coronary thrombosis, myocardial infarct, peripheral arterial diseases, arteriosclerosis and thrombosis, asthma, prophylaxis and therapy of ischaemic attacks of the CN system, shock therapy, inhibition of bronchoconstriction, inhibition of gastric acid secretion, cytoprotection of the stomach and intestinal mucosa, cytoprotection in the liver, kidneys and pancreas, reduction of pulmonary vascular resistance and of pulmonary blood pressure, promotion of kidney blood flow, use instead of heparin or as adjuvant in dialysis or hemofiltration, preservation of banked blood and thrombocytes, transplants, inhibition of labor pains, increasing cerebral blood flow, glaucoma treatment, incorporation in artificial vessels, surgical suture material, venous catheters, etc.

The 6-oxo-prostaglandin E derivatives of this invention can also be used in combination, e.g., with beta-blockers, diuretics, phosphodiesterase inhibitors, Ca antagonists, t-PA, nonsteroidal inflammation inhibitors, leucotriene synthetase inhibitors, leucotriene antagonists, thromboxane synthetase inhibitors or thromboxane antagonists.

The dose of the compounds is 1–1000 micrograms/kg/day, if they are administered to human patients. The unit dose for the pharmaceutically acceptable vehicle is 10 micrograms to 100 micrograms.

The pharmacological comparison tests, which were conducted with the compounds from examples 1 and 4 in comparison with 6-oxo-PGE$_1$, are summarized in the following table.

| Compound | Thrombocyte aggregation inhibition IC$_{50}$ | Thrombocyte shape change IC$_{50}$ | Blood Pressure reduction SH rats | Cytoprotection Stomach (rats, trauma with ethanol) |
| --- | --- | --- | --- | --- |
| 6-oxoPGE$_1$ | $7 \times 10^{-9}$ m | | dose: 10 micrograms/kg P$_s$min: 99→73 P$_D$min: 99→44 HF: 100→139 (heart frequency) | |
| Example 1 | $1.7 \times 10^{-9}$ m | $1 \times 10^{-8}$ m | dose: 3 micrograms/kg P$_s$min: 92→64 P$_D$min: 93→37 HF: 107→149 | 52% inhibition (10 micrograms/kg) |
| Example 4 | $9 \times 10^{-11}$ m | $1 \times 10^{-9}$ m | | 86% inhibition (10 micrograms/kg) |

For parenteral application, sterile, injectable aqueous or oily solutions are used. For oral application, tablets, dragees or capsules are suitable. The invention thus also relates to pharmaceutical agents based on the compounds of formula I and the usual auxiliary agents and carriers including cyclodextrin clathrates.

The active ingredients according to the invention are to be used in connection with the auxiliary agents, known and used in galenics, for example for the production of blood pressure reducers, thrombocyte aggregation inhibitors or cytoprotective agents.

EXAMPLE 1

(13E)-(11R,15S,16RS)-6,9-Di-oxo-11,15-dihydroxy-16-methyl-18,18,19,19-tetradehydro-13-prostenoic acid 160 mg of (13E)-(11R,15S,16RS)-6,9-Di-oxo-11,15-bis-(tetrahydropyran-2-yloxy)-16-methyl-18,18,19,19-tetradehydro-13-prostenoic acid was mixed with 88 ml of a mixture of acetic acid:water:tetrahydrofuran (65:35:10) and allowed to react for 15 h at room temperature. It was concentrated by evaporation in a vacuum and the residue portions of acetic acid and water were removed by addition of toluene by azeotropic vacuum distillations repeated several times. The resulting raw oil was purified by chromatography on glass plates coated with silica gel. A mixture of dichloromethane and methanol was used as mobile solvent. 108 mg (98%) the title compound was isolated as colorless oil.

IR (film): 3380, 3600-2400, 2960, 2920, 2870, 1740, 1725, 1710, 1565, 1405, 1285, 1158, 1080, 1020, 973 cm$^{-1}$

EXAMPLE 2

(13E)-(11R,15S,16RS)-6,9-Di-oxo-11,15-bis-(tetrahydropyran-2-yloxy)-16-methyl-18,18,19,19-tetradehydro-13-prostenoic acid The solution of 396 mg of (13E)-(9S,11R,15S,16RS)-6-oxo-9-hydroxy-11,15-bis-(tetrahydropyran-2-yloxy)-16-methyl-18,18,19,19-tetradehydro-13-prostenoic acid in 8 ml of absolute dimethylketone was cooled, with exclusion of moisture, to −30° C., was mixed with 270 microliters of Jones solution and stirred for 1.5 h at −30° C. to −20° C. After addition of 2 ml of isopropanol, it was poured onto 50 ml of ice water, extracted several times with a total of 100 ml of diethyl ether, washed neutral with saturated sodium chloride solution, dried on magnesium sulfate, filtered and concentrated by evaporation in a vacuum. The colorless raw oil was chromatographed on plates coated with silica gel with hexane-ethyl acetate. Besides the initial material, 160 mg (41%) of the title compound was isolated as colorless oil.

IR (film): 3600-2500, 2940, 2870, 1742, 1726, 1710, 1452, 1440, 1380, 1380, 1352, 1200, 1125 (broad), 1078, 1035, 1022, 972, 912, 870, 816 cm$^{-1}$.

The initial material was prepared as described in examples 2a to 2h.

EXAMPLE 2 a (13E)-(9S,11R,15S,16RS)-6-Oxo-9-hydroxy-11,15-bis-(tetrahydropyran-2-yloxy)-16-methyl-18,18,19,19-tetradehydro-13-prostenoic acid 690 mg of (5RS,6RS,16RS)-5-iodo-16-methyl-18,18,19,19-tetradehydro-prostaglandin I$_1$-11,15-bis-(tetrahydropyran ether)-methyl ester was dissolved in 30 ml of absolute benzene, mixed with 2.3 ml of diazabicycloundecane and heated, with exclusion of moisture, for 2 h to 50° C. The cooled solution was diluted with 60 ml of ethyl acetate, washed twice with a saturated sodium bicarbonate solution and the organic phase was dried on a mixture of magnesium sulfate and potassium carbonate. After filtering and concentration by evaporation in a vacuum the resulting raw oil was taken up in 25 ml of methanol, mixed with the solution of 600 mg of potassium hydroxide in 5 ml of water and stirred for 16 h. It was concentrated by evaporation in a vacuum to 5 ml, diluted with 70 ml of water and extracted with 50 ml of ether. The separated organic phase was rewashed with a 2n sodium hydroxide solution, the combined basic extracts were acidified with saturated citric acid to pH 4.5 and extracted several times with a total of 100 ml of trichloromethane. The organic extracts were washed neutral with saturated sodium chloride solution, dried on magnesium sulfate, filtered and concentrated by evaporation in a vacuum. 609 mg of a yellow oil was obtained which was chromatographed with ethyl acetate-isopropanol on silica gel. 396 mg (70%) of the title compound was isolated as colorless oil as main component.

IR (film): 3420, 3600-2500, 2940, 2870, 1730, 1710, 1450, 1440, 1382, 1350, 1200, 1125 (broad), 1075, 1020, 973, 908, 868, 813 cm$^{-1}$.

EXAMPLE 2 b (5RS,6RS,16RS)-5-iodo-16-methyl-18,18,19,19-tetradehydro-prostaglandin I$_1$-11,15-bis-(tetrahydropyran ether)-methyl ester The solution of 1.72 g (5E/Z,13E)-(9S,11R,15S,16RS)-9-hydroxy-11,15-bis (tetrahydropyran-2-yloxy)-16-methyl-18,18,19,19-tetradehydro-prostenoic acid-methyl ester in 50 ml of diethyl ether was mixed with the solution of 4.10 g of sodium bicarbonate in 70 ml of water, cooled to 0°-5° C. and within 90 minutes the solution of 1.77 g of iodine was instilled into 65 ml of diethyl ether. It was allowed to react for 3 more h at 0°-5° C., the excess iodine was reduced by addition of corresponding amounts of an approximate 20% sodium thiosulfate solution, the organic phase was separated and washed with absolute sodium chloride solution. After drying on magnesium sulfate, filtration and concentration by evaporation in a vacuum, 2.11 g (100%) of the title compound was isolated as yellow oil.

IR (film): 2970, 2870, 1738, 1450, 1438, 1200, 1120 (broad), 1075, 1034, 1020, 974, 907, 868, 815 cm$^{-1}$.

EXAMPLE 2 c (5E/Z,13E)-(9S,11R,15S,16RS)-9-hydroxy-11,15-bis (tetrahydropyran-2-yloxy)-16-methyl-18,18,19,19-tetradehydro-prostenoic acid-methyl ester The solution of 16.54 g of carboxybutyltriphenylphosphonium bromide in a mixture of 35 ml of absolute dimethyl sulfoxide and 15 ml of absolute tetrahydrofuran was cooled to 3° C. and mixed, with exclusion of moisture, by portions with a total of 8.0 potassium-tert-butanolate. Then the solution of 1.81 g of (1S,3RS,5R,6R,7R)-7-(tetrahydropyran-2-yloxy)-6[(13E,3S,4RS-4-methyl-3-(tetrahydropyran-2-yloxy)-1-octen-6-inyl)]-bicyclo[3.3.0]octan-3-ol was instilled in 200 ml of absolute tetrahydrofuran within 1 hour, heated to room temperature and reacted for another 30 minutes. With vigorous stirring, 200 ml of ice-cold water was poured in, adjusted with a 1N HCl to pH 3 and extracted several times with a total of 200 ml of diethyl ether. The organic phase was washed neutral with saturated sodium chloride solution, dried on magnesium sulfate and filtered off. The filtrate was mixed with a ethereal solution of diazomethane, filtered again and concentrated by evaporation in a vacuum. After chromatography of the residue on silica gel with hexane/ethyl acetate, 1.72 g (78%) of the title compound, besides traces of 5E-isomer, was isolated as colorless oil.

IR (film): 3450, 2940, 2870, 1738, 1450, 1437, 1200, 1130, 1077, 1021, 974, 907, 868, 813 cm$^{-1}$.

EXAMPLE 2 d (1S,3RS,5R,7R)-7-(tetrahydropyran-2-yloxy)-6-[(13E,3S,4RS)-4-methyl-3-(tetrahydropyran-2-yloxy)-1-octen-6-inyl)]-2-oxa-bicyclo[3.3.0]octan-3-ol At −70° C. the solution of 1.98 g of lactone in 60 ml of absolute toluene was mixed with 15 ml of a 1M solution of diisobutylaluminiumhydride in toluene and stirred for 50 minutes at −65° C. under an atmosphere of dry argon. After addition of 1.3 ml of isopropanol and then 10 ml of water, it was allowed to heat to room temperature, was suctioned off from the fine-grain precipitate and concentrated by evaporation in a water-jet vacuum. 1.81 g (91%) of a colorless oil was isolated which was reacted further without purification.

EXAMPLE 2 e (1S,5R,6R,7R)-6-[(E)-(3S,4RS)-4-methyl-3-(tetrahydropyran-2-yloxy)-oct-1-en-6-inyl]-7-(tetrahydropyran-2-yloxy)-2-oxabicyclo[3.3.0]octan-3-one The solution of 2.16 g of (1S,5R,6R,7R)-6-[(E)-3S,4RS)-3-hydroxy-4-methyl-oct-1-en-6-inyl]-7-hydroxy-2-oxa-bicyclo[3.3.0]octan-3-one in 50 ml of anhydrous methylene chloride was mixed with 1.7 ml of dihydropyran, a microspatula tip of p-toluenesulfonic acid and stirred for 30 minutes at 25° C. under an atmosphere of dry argon. It was mixed with 20 ml of a 10% aqueous bicarbonate solution, the organic phase was separated, rewashed with water and dried on magnesium sulfate. The raw product was chromatographed with a gradient system of hexane/ethyl acetate on silica gel and 2.96 g (85%) of the title compound was isolated as colorless oil.

IR (CHCl$_3$): 2945, 2870, 1767, 1452, 1440, 1352, 1261, 1182, 1128, 1074, 1020, 973, 910, 870, 869, 811 cm$^{-1}$.

EXAMPLE 2 f (1S,5R,6R,7R)-6-[(E)-(3S,4RS)-3-hydroxy-4-methyl-oct-1-en-6-inyl]-7-hydroxy-2-oxabicyclo[3.3.0]octan-3-one The solution of 4.78 g of (1S,5R,6R,7R)-6-[(E)-(3S,4RS)-3-hydroxy-methyl-oct-1-en-6-inyl]-7-benzoyloxy-2-oxabicyclo-[3.3.0]octan-3-one in 50 ml of anhydrous methanol was mixed with 2.1 g of finely powdered potassium carbonate and stirred for 5 h at 25° C. under an atmosphere of dry argon. With a 10% aqueous citric acid solution it is adjusted to pH 7, concentrated by evaporation in a vacuum to 60 ml of residual volume, mixed with 100 ml of water and extracted several times with 300 ml of dichloromethane. The combined organic phases were washed with water, dried on magnesium sulfate and concentrated by evaporation in a vacuum after filtration. The yellow raw oil was chromatographed under pressure on a silica gel column with a gradient mixture of hexane and acetone. 2.96 g (85%) of the title compound was isolated as colorless oil.

IR (film): 3350, 2960, 2870, 1760, 1640, 1435, 1420, 1350, 1180, 1075, 1020, 970, 908 cm$^{-1}$.

EXAMPLE 2 g (1S,5R,6R,7R)-6-[(E)-(3S,4RS)-3-hydroxy-4-methyl-oct-1-en-6-inyl]-7-benzoyloxy-2-oxabicyclo-[3.3.0]octan-3-one The solution of 12.5 g of (1S,5R,6R,7R)-6-[(E)-(4RS)-3-oxo-4-methyl-oct-1-en-6-inyl]-7-benzoyloxy-2-oxabicyclo[3.3.0]octan-3-one in a mixture of 300 ml and 80 ml of tetrahydrofuran is mixed, with exclusion of moisture, at −40° C. with 1.84 g of CeCl$_3$. 7H$_2$O and then in portions with a total of 1.85 g of sodium borohydride. After 1 h at −40° C. it was mixed with 50 ml of acetone and 10 ml of a 2 n H$_2$SO$_4$ and adjusted to pH 7 with 10% aqueous citric acid. It was permitted to heat to room temperature, concentrated by evaporation in a vacuum to a residual volume of 100 ml, mixed with water and extracted several times with a total of 800 ml of dichloromethane. The combined organic extracts were washed with water, dried on magnesium sulfate and concentrated by evaporation in a vacuum. 13.6 g of a yellow oil was obtained which was chromatographed under pressure on silica gel with ether/pentane. Besides small amounts of the initial material, 7.43 g (59%) of the title compound was isolated and, as more polar component (1S,5R,6R,7R)-6-[(E)-3R,4RS)-3-hydroxy-4-methyl-oct-1-en-6-inyl)]-7-benzoyloxy-2-oxabicyclo[3.3.0]octan-3-one.

IR (film): 3460, 2970, 2930, 1760, 1720, 1455, 1320, 1270, 1175, 1110, 1070, 740, 715 cm$^{-1}$.

EXAMPLE 2 h (1S,5R,6R,7R)-6-[(E)-(4RS)-3-oxo-4-methyl-oct-1-en-6-inyl]-7-benzoyloxy-2-oxabicyclo[3.3.0]octan-3-one The solution of 9.73 g of dimethyl-(2-oxo-3-methyl-hept-5-inyl)-phosphonate in 90 ml of anhydrous dimethoxyethane was instilled into a suspension of 1.75 g of NaH in 190 ml of dimethoxyethane, with exclusion of moisture. It was reacted 30 more minutes at 23° C. and at −45° C. the solution of 10.0 g of coreylactone in 150 ml of dimethoxyethane was instilled within 50 minutes. For completion of the reaction it was stirred for 3 more hours at −20° C., mixed with 3 ml of ethyl acetate, 500 ml of ether and washed several times with a saturated sodium chloride solution to neutral reaction. The organic phase was dried on magnesium sulfate, filtered and concentrated to dryness by evaporation in a vacuum. 13.2 g (98%) of the title compound was isolated as waxlike solid.

IR (CHCl$_3$): 2970, 2920, 1775, 1715, 1628, 1450, 1362, 1315, 1270, 1176, 1110, 1070, 980 cm$^{-1}$.

EXAMPLE 3

(13E)-(11R,15S,16RS)-6,9-di-oxo-11,15-dihydroxy-16-methyl-18,18,19,19-tetradehydro-13-prostenoic acid-methyl ester To 50 mg of (13E)-(11R,15S,16RS)-6,9-di-oxo-11,15-dihydroxy-16-methyl-18,18,19,19-tetradehydro-13-prostenoic acid covered with a layer of 5 ml of ether, was instilled, with vigorous stirring, an ethereal solution of diazomethane until a homogeneous solution had formed. It was concentrated by evaporation in a vacuum and the resulting raw oil was purified by preparative layer chromatography on glass plates coated with silica gel. A mixture of dichloromethane and isopropanol was used as mobile solvent. 36 mg (69%) of the title compound was isolated as colorless oil.

IR (film): 3380, 2980–2820, 1735, 1450, 1440, 1200, 1075, 1025, 975, 908 cm$^{-1}$.

EXAMPLE 4

(11R,15S,16S)-6,9-di-oxo-11,15-dihydroxy-16,20-dimethyl-13,14,18,18,19,19-hexadehydroxy-13-prostenoic acid Protection was re-moved from 410 mg of (11R,15S,16S)-6,9-di-oxo-11,15-bis-tetrahydro-pyran-2-yloxy)-16,20-dimethyl-13,14,18,18,19,19-hexadehydro-13-prostenoic acid analogously to example 1. After chromatographic purification, 236 (82%) of the title compound was isolated as colorless oil.

IR (film): 3400, 3600 to 2500, 2980, 2230, 1740, 1730, 1710, 1570, 1410, 1280, 1160, 1075, 1020, 970 cm$^{-1}$.

EXAMPLE 5

(11R,15S,16S)-6,9-di-oxo-11,15-bis-(tetrahydropyran-2-yloxy)-16,20-dimethyl-13,14,18,18,19,19-hexadehydro-13-prostenoic acid 628 mg of (9S,11R,15S,16S)-6-oxo-9-hydroxy-11,15-bis-(tetrahydropyran-2-yloxy)-16,20-dimethyl-13,14,18,18,19,19-hexadehydro-13-prostenoic acid is oxidized analogously to the process with Jones solution cited in example 2. After the appropriate chromatographic purification was performed, 458 mg (73%) of the title compound was obtained as colorless oil.

IR (film): 3600 to 2500, 2940, 2870, 2230, 1742, 1730, 1700, 1450, 1440, 1380, 1352, 1320, 1280, 1260, 1200, 1180, 1150, 1125, 1075, 1034, 1020, 968, 910, 868, 815 cm$^{-1}$.

The initial material was prepared as described in examples 5a to 5i.

EXAMPLE 5a (9S,11R,15S,16S)-6-oxo-9-hydroxy-11,15-bis-(tetrahydropyran-2-yloxy)-16,20-dimethyl-13,14,18,18,19,19-hexadehydro-13-prostenoic acid 100 mg of (5RS,6RS,16S)-5-iodo-16,20-dimethyl-13,14,18,18,19,19-hexadehydro-prostaglandin I$_1$-11,15-bis-(tetrahydropyranyl ether)-methyl ester was reacted in complete analogy with example 2a and purified. 630 mg (77%) of the title compound was isolated as yellow oil.

IR (film): 3500 to 2500, 2940, 2870, 2230, 1732, 1709, 1450, 1440, 1380, 1354, 1320, 1200, 1117, 1076, 1035, 1020, 970, 908, 870, 815 cm$^{-1}$.

EXAMPLE 5 b (5RS,6RS,16S)-5-iodo-16,20-dimethyl-13,14,18,18,19,19-hexahydro-prostaglandin I$_1$-11,15-bis-(tetrahydropyranyl ether)-methyl ester 1.03 g (5Z)-(9S,11R,15S,16S)-9-hydroxy-11,15-bis-(tetrahydropyran-2-yloxy)-16,20-dimethyl-13,14,18,18,19,19-hexadehydro-prostadienoic acid-methyl ester was reacted analogously to example 2b. After the appropriate working up was performed, 1.24 g (98%) of the title compound was isolated as yellow oil.

IR (film): 2940, 2870, 2230, 1738, 1450, 1438, 1352, 1320, 1200, 1118, 1076, 1035, 1020, 972, 908, 870, 817 cm$^{-1}$.

EXAMPLE 5c (5Z)-(9S,11R,15S,16S)-9-hydroxy-11,15-bis-(tetrahydropyran-2-yloxy)-16,20-dimethyl-13,14,18,18,19,19-hexadehydroprostadienoic acid-methyl ester 2.39 g of (5Z,13E)-(9S,11R,15S,16S)-9-hydroxy-11,15-bis-(tetrahydropyran-2-yloxy)-14-bromo-16,20-dimethyl-18,18,19,19-tetradehydro-prostadienoic acid-methyl ester was dissolved in a mixture of 11 ml of anhydrous THF and 26 ml of anhydrous dimethyl sulfoxide, mixed with 1.23 g of potassium tert-butanolate and stirred for 5 hours at 25° C. under an atmosphere of dry argon. It was poured into ice water, acidified with a 10% citric acid solution, extracted several times with diethyl ether and the combined organic extracts were dried on magnesium sulfate. After filtering and evaporation of the solvent in a vacuum, 2.01 g (00%) of (5Z)-(9S,11R,15S,16S)-9-hydroxy-11,15-bis-(tetrahydropyran-2-yloxy)-16,20-dimethyl-13,14,18,18,19,19-hexadehydro-prostadienoic acid was isolated, which, without further purification, was esterified with a ethereal solution of diazomethane analogously to example 2c. The residue was chromatographed under pressure on silica gel with hexane/ethyl acetate and 1.22 g (58%) of the title compound was isolated as colorless oil.

IR (film): 3500 (broad), 2940, 2870, 2230, 1738, 1452, 1436, 1373, 1354, 1320, 1240, 1200, 1130, 1076, 1020, 970, 908, 870, 816 cm$^{-1}$.

EXAMPLE 5 d (5Z,13E)-(9S,11R,15S,16S)-9-hydroxy-11,15-bis(tetrahydropyran-2-yloxy)-14-bromo-16,20-dimethyl-18,18,19,19-tetradehydro-prostadienoic acid methyl ester 2.53 g of (1S,3RS,5R,6R,7R)-6-[(E)-(3S,4S)-2-bromo-3-(tetrahydropyran-2-yloxy)-4-methyl-non-1-en-6-inyl]-7-(tetrahydropyran-2-yloxy)-2-oxa-bicyclo[3.3.0]octan-3-ol was subjected analogously to example 2c to Witting reaction conditions and then to esterification conditions with diazomethane. After chromatographic purification, 2.40 g (80%) of the title compound was isolated as colorless oil.

IR (film): 3460 (broad), 2940, 2870, 1738, 1650, 1450, 1438, 1374, 1350, 1338, 1320, 1240, 1200, 1128, 1115, 1076, 1052, 1020, 970, 908, 870, 815, 736 cm$^{-1}$.

EXAMPLE 5 e (1S,3RS,5R,6R)-6-[(E)-(3S,4S)-2-bromo-3-(tetrahydropyran-2-yloxy)-4-methyl-non-1-en-6-inyl]-7-(tetrahydropyran-2-yloxy)-2-oxa-bicyclo[3.3.0]octan-3-ol 2.77 g of (1S,3RS,5R,6R,7R)-6-[(E)-(3S,4S)-2-bromo-3-(tetrahydropyran-2-yloxy)-4-methyl-non-1-en-6-inyl]-7-(tetrahydropyran-2-yloxy)-2-oxa-bicyclo[3.3.0]-octan-3-one was reduced analogously to example 2 d. After working up and chromatographic purification, 2.54 g (91%) of the title compound was isolated as colorless oil.

IR (film): 3400 (broad), 2940, 2870, 1736, 1648, 1452, 1440, 1375, 1352, 1340, 1322, 1260, 1200, 1184, 1120, 1070, 1020, 970, 908, 868, 815 cm$^{-1}$.

EXAMPLE 5 f (1S,5R,6R,7R)-6-[(E)-(3S,4S)-2-bromo-3-(tetrahydropyran-2-yloxy)-4-methyl-non-1-en-6-inyl]-7-(tetrahydropyran-2-yloxy)-2-oxa-bicyclo[3.3.0]octan-3-one 2.00 g of (1S,5R,6R,7R)-6-[(E)-(3S,4S)-2-bromo-3-hydroxy-4-methyl-non-1-en-6-inyl]-7-hydroxy-2-oxa-bicyclo[3.3.0]octan-3-one was reacted analogously to example 2 e. After chromatographic purification, 2.78 g (96%) of the title compound was isolated as colorless oil.

IR (film): 2970, 2930, 1770, 1640, 1450, 1430, 1360, 1335, 1235, 1120, 1070, 1025, 910, 868, 812 cm$^{-1}$.

EXAMPLE 5 g (1S,5R,6R,7R)-6-[(E)-(3S,4S)-2-bromo-3-hydroxy-4-methyl-non-1-en-6-inyl]-7-hydroxy-2-oxa-bicyclo-[3.3.0]octan-3-one 3.12 g of (1S,5R,6R,7R)-6-[(E)-(3S,4S)-2-bromo-3-hydroxy-4-methyl-non-1-en-6-inyl]-7-benzoyloxy-2-oxa-bicyclo[3.3.0]octan-3-one was dissolved in 18 ml of p.A. methanol, mixed with 290 mg of a finely powdered potassium carbonate and stirred for 3 h at 25° C. It was adjusted to pH 7 by addition of a 50% hydrochloric acid and concentrated by evaporation in a water-jet vacuum at 30° C. The residue was taken up in methylene chloride, filtered over magnesium sulfate and Celite, again concentrated by evaporation in a water-jet vacuum and chromatographed under pressure on about 200 ml of fine silica gel using a gradient of hexane/ethyl acetate. 2.00 g (82%) of the title compound was isolated as colorless oil.

IR (film): 3400, 2950, 2910, 1755, 1640, 1440, 1415, 1340, 1300, 1180, 1075, 1030, 968, 905 cm$^{-1}$.

EXAMPLE 5 h (1S,5R,6R,7R)-6-[(E)-(3S,4S)-2-bromo-3-hydroxy-4-methyl-non-1-en-6-inyl]-7-benzoyloxy-2-oxa-bicyclo[3.3.0]-octan-3-one 16.7 g of (1S,5R,6R,7R)-6-[(E)-(4S)-2-bromo-3-oxo-4-methyl-non-1-en-6-inyl]-7-benzoyloxy-2-oxa-bicyclo[3.3.0]-octan-3-one was reduced analogously to example 2 g. After chromatographic purification, 4.1 g (24%) of the title compound as well as 6.6 g of (1S,5R,6R,7R)-6-[(E)-(3S,4S)-2-bromo-3-oxo-4-methyl-non-1-en-6-inyl]-7-benzoyloxy-2-oxa-bicyclo[3.3.0]octan-3-one (39%) were isolated.

IR (film): 3460 (broad), 3060, 2970, 2930, 1770, 1714, 1602, 1450, 1317, 1272, 1178, 1115, 1070, 1026, 737, 715 cm$^{-1}$.

EXAMPLE 5 i (1S,5R,6R,7R)-6-[(E)-(4S)-s-bromo-3-oxo-4-methyl-non-1-en-6-inyl]-7-benzoyloxy-2-oxa-bicyclo[3.3.0]octan-3-one A solution of 13.7 g of dimethyl-[(3S)-2-oxo-3-methyl-oct-5-inyl]phosphonate in 135 ml of dimethoxyethane was instilled at 0° C., with exclusion of moisture, in a suspension of 2.58 g of NaH in 225 ml of dimethoxyethane. After 20-minutes stirring, the now clear solution was mixed with 9.89 g of finely powdered N-bromosuccinimide, stirred for 1 h more at 0° C., the solution of 12.3 coreylactone was instilled and reacted for 2 more hours at 0° C. It is allowed to flow under vigorous stirring into 800 ml a 10% aqueous ammonium choloride solution, was extracted several times with a total of 1.5 liters of diethyl ether, the organic phase was re-washed with water, dried on magnesium sulfate and, after filtering and concentration by evaporation in a vacuum, 27.4 g of a yellow raw oil was isolated, which was chromatographically purified under pressure by a gradient of hexane and ethyl acetate. 16.9 g (72%) of the title compound was isolated as colorless oil.

IR (film): 2970, 2920, 1765, 1720, 1600, 1450, 1360, 1315, 1270, 1170, 1105, 1070, 965 cm$^{-1}$.

EXAMPLE 6

(11R,15S,16S)-6,9-di-oxo-11,15-dihydroxy-16,20-dimethyl-13,14,18,18,19,19-hexadehydro-13-prostanoic acid-methyl ester An ethereal solution of diazomethane was instilled at 0° to 5° C. to a vigorously stirred emulsion of 63 mg of (11R,15S,16S)-6,9-di-oxo-11,15-dihydroxy-16,20-dimethyl-13,14,18,18,19,19-hexadehydro-13 prostenoic acid in 10 ml of ether. Working up and purification took place analogously to example 3. 46 mg (70%) of the title compound was isolated as colorless oil.

IR (film): 3400, 2980–2820, 2230, 1737, 1450, 1440, 1200, 1078, 1020, 970, 910 cm$^{-1}$.

We claim:

1. A 6-oxo-prostaglandin $E_1$ derivative of formula I,

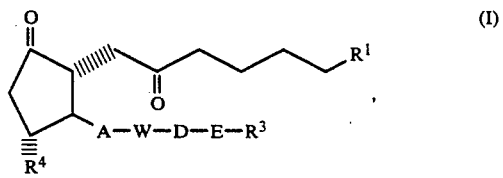

wherein $R^1$ is the radical $COOR^2$ wherein $R^2$ is a hydrogen atom, a $C_1$–$C_{10}$ alkyl, a $C_5$–$C_6$ cycloalkyl or a $C_6$–$C_{10}$ aryl group or a 5- or 6-membered heterocyclic radical, having at least one O, N or S heteroatom, A is an E-configured CH=CH or a —C≡C— group, W is a free or functionally modified hydroxymethylene group or a free or functionally modified

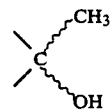

group, and the OH group in each case can be in the alpha or beta position,

D is a branched-chain alkylene group with 2-5 C atoms,

E is a —C≡C— group, $R^3$ is $C_1$–$C_{10}$ alkyl, $C_3$–$C_{10}$ cycloalkyl or an optionally substituted $C_6$–$C_{10}$ aryl group or a 5- or 6-membered heterocyclic group, having at least one O, N or S heteroatom, $R^4$ is a free or functionally modified hydroxy group, or if $R^2$ is a hydrogen atom, a salt thereof with a physiologically compatible base, or an alpha, beta or gamma cyclodextrin clathrate thereof, with the proviso that the 16-position (prostanoic acid nomenclature) is substituted by alkyl.

2. A compound of claim 1, which is 16-methyl.

3. A compound of claim 1, wherein —C≡C— is in the 18-position (prostanoic acid nomenclature).

4. A compound of claim 2, wherein —C≡C— is in the 18-position (prostanoic acid nomenclature).

5. (13E)-(11R,15S,16RS)-6,9-Di-oxo-11,15,-dihydroxy-16-methyl-18,18,19,19-tetradehydro-13-prostenoic acid,
(13E)-(11R,15S,16RS)-6,9-di-oxo-11,15,-dihydroxy-16-methyl-18,18,19,19-tetradehydro-13-prostenoic acid-methyl ester,
(11R,15S,16S)-6,9-di-oxo-11,15,-dihydroxy-16,20-dimethyl-13,14,18,18,19,19-hexadehydro-13-prostenoic acid, and
(11R,15S,16S)-6,9-di-oxo-11,15-bis-(tetrahydropyran-2-yloxy)-16,20-dimethyl-13,14,18,18,19,19-hexadehydro-13-prostanoic acid,
(1S,5R,6R,7R)-6-[(E)-(4S)-2-bromo-3-oxo-4-methyl-non-1-en-6-inyl]-7-benzoyloxy-2-oxa-bicyclo[3.3.0]octan-3-one, each a compound of claim 1.

6. A pharmaceutical composition, comprising an effective amount of one or more compounds of claim 1 and one or more customary auxiliary agents and carriers.

7. A method of reducing blood pressure, comprising administering an effective amount of a compound of claim 4.

8. A method of inhibiting thrombocyte aggregation, comprising administering an effective amount of a compound of claim 4.

* * * * *